United States Patent [19]

Pugach

[11] 4,251,458
[45] Feb. 17, 1981

[54] PROCESS FOR PREPARING CARBOXYLIC ACID ANHYDRIDES

[75] Inventor: Joseph Pugach, Ho-Ho-Kus, N.J.

[73] Assignee: Halcon Research and Development Corporation, New York, N.Y.

[21] Appl. No.: 81,304

[22] Filed: Oct. 2, 1979

[51] Int. Cl.³ .................. C07C 51/54; C07C 51/56
[52] U.S. Cl. ................................ 260/546; 260/549
[58] Field of Search ........................ 260/546, 549

[56] References Cited

U.S. PATENT DOCUMENTS

| | | | |
|---|---|---|---|
| 2,729,651 | 1/1956 | Reppe et al. | 260/546 X |
| 2,730,546 | 1/1956 | Reppe et al. | 260/549 |
| 2,789,137 | 4/1957 | Reppe et al. | 260/546 |
| 3,927,078 | 12/1975 | Lapporte et al. | 260/546 X |
| 3,989,751 | 11/1976 | Forster et al. | 260/546 |
| 4,002,677 | 1/1977 | Naglieri et al. | 260/549 |
| 4,002,678 | 1/1977 | Naglieri et al. | 260/549 |
| 4,046,807 | 9/1977 | Kuckertz | 260/549 |
| 4,115,444 | 9/1978 | Rizkalla | 260/549 |

*Primary Examiner*—Howard T. Mars
*Assistant Examiner*—Vera C. Clarke
*Attorney, Agent, or Firm*—William C. Long; David Dick; Riggs T. Stewart

[57] ABSTRACT

A carboxylic acid anhydride, such as acetic anhydride, is prepared from a carboxylate ester or a hydrocarbyl ether in carbonylation processes comprising the use of a halide, carbon monoxide and a Group VIII noble metal in the presence of promoters comprising at least one metal of Group VIB of the Periodic Table, or their compounds, and an arsine of the formula

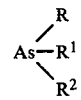

wherein R and R¹ are monocyclic aryl groups or alkyl groups and R² is the radical

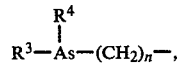

a monocyclic aryl group or an alkyl group, and wherein R³ and R⁴ are each a monocyclic aryl group or an alkyl group, with the proviso that at least one of R, R¹ and R² is a monocyclic aryl group, n being zero or a digit from 1–20.

10 Claims, No Drawings

PROCESS FOR PREPARING CARBOXYLIC ACID ANHYDRIDES

This invention relates to the preparation of the anhydrides of carboxylic acids, more particularly monocarboxylic acids, and especially the anhydrides of lower alkanoic acids, such as acetic anhydride, by carbonylation.

Acetic anhydride has been known as an industrial chemical for many years and large amounts are used in the manufacture of cellulose acetate. It has commonly been produced on an industrial scale by the reaction of ketene and acetic acid. It is also known that acetic anhydride can be produced by the decomposition of ethylidene diacetate, as well as by the oxidation of acetaldehyde, for example. Each of these "classic" processes has well-known drrawbacks and disadvantages and the search for an improved process for the production of acetic anhydride has been a continuing one. Proposals for producing anhydrides by the action of carbon monoxide upon various reactants (carbonylation) have been described, for example, in Reppe et al. U.S. Pat. Nos. 2,729,561, 2,730,546 and 2,789,137. However, such prior proposals involving carbonylation reactions have required the use of very high pressure. Carbonylation at lower pressures has been proposed but as a route to the preparation of acetic acid. French Pat. No. 1,573,130, for example, describes the carbonylation of methanol and mixtures of methanol with methyl acetate in the presence of compounds of iridium, platinum, palladium, osmium and ruthenium and in the presence of bromine or iodide under more moderate pressures than those contemplated by Reppe et al. Similarly, South African Pat. No. 68/2174 produces acetic acid from the same reactants using a rhodium component with bromine or iodine components. Schultz (U.S. Pat. Nos. 3,689,533 and 3,717,670) has disclosed a vapor-phase process for acetic acid production employing various catalysts comprising a rhodium component dispersed on a carrier.

More recently, Belgian Pat. No. 819,455 shows the carbonylation of certain esters and/or ethers to produce carboxylic acid anhydrides employing Group VIII noble metal catalysts in the presence of bromine or iodine moieties optionally in the presence of promotors comprising at least one metal which is an element having an atomic weight greater than 5 of Groups IA, IIA, IIIA, IVB, and VIB, a non-noble metal of Group VIII or a metal of the lanthanide and actinide groups of the Periodic Table, and their compounds. U.S. Pat. No. 3,927,078 shows the preparation of acetic anhydride by the carbonylation of methyl acetate or dimethyl ether in the presence of a Group VIII noble metal compound and in the presence of an iodide or bromide promoter and is characterized by the inclusion of a proton donor in the reaction system. The optional use of Lewis acids is also disclosed. U.S. Pat. No. 4,046,807 of Sept. 6, 1977 also shows the carbonylation of methyl acetate to produce acetic anhydride using noble metal compound catalysts and iodides and shows the use of triphenylphosphine as a promoter along or in combination with cobalt acetate.

More recently, U.S. Pat. No. 4,115,444 dated Sept. 19, 1978 discloses an improved process for preparing carboxylic acid anhydrides, including acetic anhydride, wherein specified esters and/or ethers are carbonylated in the presence of Group VIII noble metals or their compounds in a system containing an iodide or a bromide and in the presence of a promoter of at least one metal of Groups IVB, VB and VIB or a non-noble metal of Group VIII, or their compounds, in combination with an organo-nitrogen compound or an organophosphorus compound wherein the nitrogen and phosphorus are trivalent.

It is an object of the present invention to provide a further improved process for the manufacture of carboxylic acid anhydrides, especially lower alkanoic anhydrides, such as acetic anhydride and, in particular, to provide an improvement in the process of U.S. Pat. No. 4,115,444.

In accordance with the invention, a carboxylic ester and/or a hydrocarbyl ether are carbonylated under substantially anhydrous conditions in the presence of a Group VIII nobel metal catalyst, in the presence of a halide which is an iodide or a bromide and in the presence of promoters comprising at least one metal of Group VIB, or their compounds, in combination with an arsine of the formula

wherein R and $R^1$ are monocyclic aryl groups or alkyl groups and $R^2$ is the radical

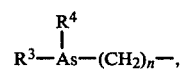

a monocyclic aryl group or an alkyl group, and wherein $R^3$ and $R^4$ are each a monocyclic aryl group or an alkyl group, with the proviso that at least onne of R, $R^1$ and $R^2$ is a monocyclic aryl group, n being zero or a digit from 1–20. The alkyl groups in the foregoing formula are preferably lower alkyl groups of 1–8 carbon atoms, such as methyl, ethyl, propyl, butyl, hexyl and octyl, especially 1–4 carbon atoms, but may contain as many as 20 carbon atoms. Similarly, the aryl group is preferably phenyl but may be phenyl substituted with one or more alkyl groups containing one or more carbon atoms, e.g. up to 6 carbon atoms, such as methyl, ethyl, propyl, butyl, and hexyl. The phenyl groups can also be substituted with other nonreactive substituents such as halo, e.g., chloro, or cyano, and the like. Typical examples of the arsines used in the process of this invention include triphenylarsine, tri-p-tolylarsine, dimethylphenylarsine, methyldiphenylarsine, methylditolylarsine, dimethylchlorophenylarsine, dimethylcyanophenylarsine, bis-(diphenylarsino) methane, bis-(diphenylarsino) ethane, bis-(diphenylarsino) propane, bis-(diphenylarsino) butane, tetraphenyl bi-arsine, and the like. Particularly preferred are the alkyl diaryl arsines, especially methyldiphenylarsine.

It has been discovered that this catalyst-multiple promoter system makes possible surprisingly increased reaction rates. The rate of reaction and the product concentration per unit of time realized from this catalyst-multiple promoter combination have been found to be unexpectedly exceptionally high. Belgian Pat. No. 839,321 shows a process for the preparation of ethylidene diacetate by the reaction of carbon monoxide and hydrogen upon methyl acetate or dimethyl ether using a Group VIII noble metal catalyst in the presence of an iodide or bromide and in the presence of a promoter which may be a phosphine, an arsine or a stibine. In some cases, acetic anhydride is produced as a by-product. In accordance with the present invention, however, it has been discovered that arsines of a particular character, i.e., those falling within the formula set forth above, exhibit outstanding characteristics not shared by other arsines or by phosphines and stibines, particularly in terms of activity which is expressed as reaction rate.

In carrying out the process of the present invention, carbon monoxide is reacted with a carboxylate ester, especially a lower alkyl alkanoate, or a hydrocarbyl ether such as a lower alkyl ether, to produce a carboxylic anhydride such as a lower alkanoic anhydride, the carbonylation taking place in the presence of an iodide or bromide, e.g., a hydrocarbyl halide, especially a lower alkyl halide, which is an iodide or bromide, such as methyl iodide. Thus, acetic anhydride for example, can be effectively prepared in a representative case by subjecting methyl acetate or dimethyl ether to carbonylation in the presence of methyl iodide. In all cases, the carbonylation is carried out under substantially anhydrous conditions in the presence of the catalyst-multiple promoter system described above. As indicated, an ester-ether mixture can be carbonylated if desired.

It will be understood that the hydrocarbyl halide may be formed in situ and the halide may thus be supplied to the system not only as the hydrocarbyl halide but the halogen moiety may also be supplied as another organic halide or as the hydrohalide or other inorganic halide, e.g., a salt, such as the alkali metal or other metal salts, or even as elemental iodine or bromide. Following the reaction the organic components of the reaction mixture are readily separated from one another, as by fractional distillation.

In like manner, other lower alkanoic anhydrides, i.e., anhydrides of lower alkanoic acids, such as propionic anhydride, butyric anhydrides and valeric anhydrides, can be produced by carbonylating the corresponding lower alkyl alkanoate or lower alkyl ether. Similarly, other carboxylic acid anhydrides, e.g., the anhydrides of other alkanoic acids, such as those containing up to 12 carbon atoms, for example capric anhydrides, caprylic anhydrides and lauric anhydrides, and like higher anhydrides are produced by carbonylating the corresponding ester, e.g., alkyl alkanoates containing up to 11 carbon atoms in the alkyl group and up to 12 carbon atoms in the carboxylate group or aryl esters, or the corresponding ether, such as heptyl caprylate, nonyl decanoate, undecyl laurate, phenyl benzoate, heptyl ether, nonyl ether, dibenzyl ether, and the like.

It is preferred that the reactants be selected so that the resulting anhydride will be a symmetrical anhydride, i.e., having two identical acyl groups, viz, wherein R in equations (1) and (2) is the same in each instance, but it is within the scope of the invention to produce non-symmetrical or mixed anhydrides and this can be readily effected by using different combinations of reactants, e.g., by using compounds having different R groups in the foregoing reactions, as will be obvious to persons skilled in the art.

The above-described reactions can be expressed as follows:

  (1)

  (2)

wherein R is a hydrocarbyl radical which may be saturated, e.g., alkyl, of 1 to 11 carbon atoms, or monocylic aryl, e.g., phenyl, or aralkyl, e.g., benzyl. Preferably, R is lower alkyl, i.e., an alkyl group of 1 to 4 carbon atoms, such as methyl, ethyl, n-propyl, i-propyl, n-butyl, sec-butyl, and t-butyl.

The hydrocarbyl radical may be substituted with substituents which are inert in the reactions of the invention. The more volatile alkyl halide and any unreacted ether or ester which are present in the final reaction mixture can be readily removed, as by distillation, for recycling, and the net yield of product is substantially exclusively the desired carboxylic anhydride. In the case of liquid-phase reaction, which is preferred, the organic compounds are easily separated from the metal-containing components, as by distillation. The reaction is suitably carried out in a reaction zone to which the carbon monoxide, the ester or ether, the halide and the noble metal catalyst and the promoters are fed. No water is produced in the above-described reactions and anhydrous or substantially anhydrous conditions are employed.

In carrying out the process of the invention, a wide range of temperatures, e.g., 25° to 350° C. are suitable but temperatures of 100° to 250° C. are preferably employed and the more preferred temperatures generally lie in the range of 125° to 225° C. Temperatures lower than those mentioned can be used but they tend to lead to reduced reaction rates, and higher temperatures may also be employed but there is no particular advantage in their use. The time of reaction depends largely upon the temperature employed. The reaction is carried out under superatmospheric pressure but excessively high pressures, which require special high-pressure equipment, are not necessary. In general, the reaction is effectively carried out by employing a carbon monoxide partial pressure which is preferably 15 to 1,000 p.s.i., and most preferably 30 to 700 p.s.i., although carbon monoxide partial pressures of 1 to 10,000 p.s.i. can also be employed. By maintaining the partial pressure of carbon monoxide at the values specified, adequate amounts of this reactant are always present. The total pressure is preferably that required to maintain the liquid phase and in this case the reaction can be advantageously carried out in an autoclave or similar apparatus. Preferably, the reaction product is introduced into a distillation zone, which may be a fractional distillation column, or a series of columns, effective to separate the hydrocarbyl halide and the ester or ether, free organic promoter and the product anhydride. The boiling points of these several compounds are sufficiently far apart that their separation by conventional distillation presents no particular problem. Likewise, the higher boiling organic components can be readily distilled away from the noble metal catalyst, the metal-containing promoter, and any organic promoter which may be in the form of a relatively non-volatile complex. The hydrocarbyl halide and the noble metal catalyst and the promoters, can then be combined with fresh amounts of ester or ether and carbon monoxide and reacted to produce additional quantities of anhydride.

The ratio of ester or ether to the halide in the reaction system can vary over a wide range. Typically, there are used 0.1 to 1,000 mols of the ester or ether per mol of halide, preferably 1 to 30 mols per mol.

The process is advantageously carried out in the presence of a solvent or diluent, particularly when the reactant has a relatively low boiling point, as in the case of dimethyl ether. The presence of a higher boiling solvent or diluent, which may be the product anhydride itself, e.g., acetic anhydride in the case of dimethyl ether, or which may be the corresponding ester, e.g., methyl acetate, again in the case of methyl ether, will make it possible to employ more moderate total pressure. Alternatively, the solvent or diluent may be any organic solvent which is inert in the environment of the process such as hydrocarbons, e.g., octane, benzene, toluene, or carboxylic acids, e.g., acetic acid, and the like. The carboxylic acid, when used, should pre correspond to the anhydride being produced. A solvent or diluent is suitably selected which has a boiling point sufficiently different from the desired product in the reaction mixture so that it can be readily separated, as will be apparent to persons skilled in the art.

The Group VIII noble metal catalyst, i.e., iridium, osmium, platinum, palladium, rhodium and ruthenium, can be employed in any convenient form, viz., in the zero valent state or in any higher valent form. For example, the catalyst to be added may be the metal itself in finely divided form, or as a metal carbonate, oxide, hydroxide, bromide, iodide, chloride, lower alkoxide (methoxide), phenoxide or metal carboxylate wherein the carboxylate ion is derived from an alkanoic acid of 1 to 20 carbon atoms. Similarly, complexes of the metals can be employed, for example the metal carbonyls, such as iridium carbonyls and rhodium carbonyls, e.g., hexarhodium hexadecacarbonyl, or as other complexes such as the carbonyl halides, e.g., iridium tri-carbonyl chloride [Ir(CO)$_3$Cl])$_2$ or chlorodicarbonyl rhodium dimer, or the acet cetonates, e.g., rhodium acetylacetonate Rh(C$_5$H$_7$O$_2$)$_3$. Included among the catalysts listed above are complexes of the Group VIII noble metal with organic promoter ligands derived from the arsine promoters hereinabove described. It will be understood that the foregoing compounds and complexes are merely illustrative of suitable forms of the Group VIII noble metal catalyst and are not intended to be limiting.

The carbon monoxide is preferably employed in substantially pure form, as available commercially, but inert diluents such as carbon dioxide, nitrogen, methane, and noble gases can be present if desired. The presence of inert diluents does not affect the carbonylation reaction but their presence makes it necessary to increase the total pressure in order to maintain the desired CO partial pressure. The carbon monoxide, like other reactants should, however, be essentially dry, i.e., the CO and the other reactants should be reasonably free from water. The presence of minor amounts of water such as may be found in the commercial forms of the reactants is, however, entirely acceptable. Hydrogen which may be present in very small amounts as an impurity is not objectionable and even may tend to stabilize the catalyst.

In accordance with the invention, the activity of the Group VIII noble metal catalysts described above is significantly improved, particularly with respect to reaction rate and product concentration, catalyst stability and corrosion inhibition, by the concurrent use of a promoter combination or co-promoter system containing a metal component which is a metal of Group VIB of the Periodic Table in association or combination with an aryl or a mixed alkyl aryl arsine of the character described above. Most preferred is chromium. The promoters may be used in their elemental form, e.g., as finely-divided or powdered metals, or they may be employed as compounds of various types, both organic and inorganic, which are effective to introduce the element into the reaction system. Thus, typical compounds of the promoter elements include oxides, hydroxides, halides, e.g., bromides and iodides, oxyhalides, hydrides, alkoxides, and the like. Especially preferred organic-metal compounds are the salts of organic mono-carboxylic acids, e.g., alkanoates such as acetates, butyrates, decanoates, laurates, benzoates, and the like. Other compounds include the metal alkyls and carbonyl compounds as well as chelates, association compounds and enol salts. Particularly preferred are the carbonyls, compounds which are bromides or iodides, and organic salts, e.g., salts of the mono-carboxylic acid corresponding to the anhydride being produced. Mixtures of promoters can be used, if desired. The exact mechanism of the effect of the promoter, or the exact form in which the promoter acts, is not known but it has been noted that when the promoter is added in elemental form, e.g., as a finely-divided metal, a slight induction period is observed.

The metals employed may contain impurities normally associated with the commercially available metal or metal compounds, and need not be purified any further. Thus, the commercially available metal or metal compound is suitably employed in the case of the Group VIII noble metal catalyst and in the case of the metal promoter.

Although it is preferred that the arsine promoters be added separately to the catalyst system, it is possible to add them as complexes with the Group VIII noble metal such as chlorotris-(triphenylarsine) rhodium, chlorocarbonyl (tripenylarsine) rhodium, hydridocarbonyltris-(triphenylarsine) rhodium, the corresponding methyldiphenylarsine compounds, trichlorocarbonyl-bis-(triphenylarsine) rhodium, and trichlorocarbonyl-bis-(methyldiphenylarsine) rhodium, and the like. Both free arsine promoters and complexed promoters can also be used. Indeed, when a complex of the arsine promoter and the Group VIII noble metal is used, free arsine promoter may be added as well, if desired.

The amount of Group VIII noble metal catalyst is in no way critical and is not a parameter of the process of the invention and can vary over a wide range. As is well known to persons skilled in the art, the amount of catalyst used is that which will provide the desired suitable and reasonable reaction rate. However, essentially any amount of catalyst will facilitate the basic reaction and can be considered a catalytically-effective quantity. Typically, however, the catalyst is employed in the amount of 1 mol per 10 to 100,000 mols of ester or ether, preferably 1 mol per 100 to 10,000 mols of ester or ether, and most preferably 1 mol per 500 to 2,000 mols of ester or ether.

The quantity of metal promoter can vary widely. Typically, it is one mol per 10,000 mols of ester or ether, preferably it is used in the amount of 1 mol per 20 to 2,000 mols most preferably 1 mol per 50 to 500 mols of ester or ether. The quantity of arsine promoter can also vary widely but typically it is used in the amounts of 1 mol per 1 to 10,000 mols of ester or ether, preferably 1 mol per 10 to 1,000, most preferably 15 to 200 mols of ester or ether.

In the working up of the reaction mixtures, e.g., by distillation, as discussed above, the metal promoter generally remains with the Group VIII noble metal catalyst, i.e., as one of the least volatile components, and is suitably recycled or otherwise handled along with the catalyst. The organic promoter can also be recovered and recycled.

It will be apparent that the above-described reactions lend themselves readily to continuous operation in which the reactants and catalyst, preferably in combination with the promoter combination, are continuously supplied to the appropriate reaction zone and the reaction mixture continuously distilled to separate the volatile organic constituents and to provide a net product consisting essentially of carboxylic acid anhydride, with the other organic components being recycled and, in the case of liquid-phase reaction, a residual Group VIII noble metal-containing (and promoter-containing) fraction also being recycled. In the case of such continuous operation, it will be apparent that the halogen moiety remains in the system at all times subject only to occasional handling losses or purges. The small amount of halogen makeup which may be needed from time to time is preferably effected by supplying the halogen in the form of the hydrocarbyl halide but, as pointed out above, the halogen moiety may also be supplied as another organic halide or as the hydrogen halide or other inorganic halide, e.g., a salt, such as the alkali metal or other metal salts, or as elemental iodine or bromine.

As previously indicated, the carbonylation reaction involved in the process of the invention can be carried out in the vapor phase, if desired, by appropriate control of the total pressure in relation to the temperature so that the reactants are in vapor form when in contact with the catalyst. In the case of vapor-phase operation, and in the case of liquid-phase operation, if desired, the catalyst and promoter, i.e., the catalyst components, may be supported, i.e., they may be dispersed on a carrier of conventional type such as alumina, silica, silicon carbide, zirconia, carbon, bauxite, attapulgus clay, and the like. The catalyst components can be applied to the carriers in conventional manner, e.g., by impregnation of the carrier with a solution of the catalyst, or the catalyst and promoter, followed by drying. Catalyst component concentrations upon the carrier may vary widely, e.g., 0.01 weight percent to 10 weight percent, or higher. The organic promoter can be either fed with the reactants or complexed with the catalyst. Typical operating conditions for vapor-phase operation are a temperature of 100° to 350° C., preferably 150° to 275° C. and most preferably 175° to 225° C., a pressure of 1 to 5,000 p.s.i.a., preferably 50 to 1,500 p.s.i.a. and most preferably 150 to 500 p.s.i.a., with space velocities of 50 to 10,000 hr.$^{-1}$, preferably 200 to 6,000 hr.$^{-1}$ and most preferably 500 to 4,000 hr.$^{-1}$(STP).

The following examples will serve to provide a fuller understanding of the invention, but it is to be understood that they are given for illustrative purposes only, and are not to be construed as limitative of the invention. In the examples, all percentages are by weight, unless otherwise indicated.

In the examples, the various reactants and catalyst components are charged to the reaction vessel which is then closed and brought to the reaction temperature indicated. The initial carbon monoxide partial pressure specified is the calculated value at reaction temperature at the beginning of the reaction, i.e., at zero conversion. The total pressure is maintained by introducing additional carbon monoxide as the reaction proceeds.

EXAMPLE I

Methyl acetate containing 0.01 mol per liter of rhodium trichloride hydrate, 0.6 mol per liter of methyl iodide, 0.02 mol per liter of chromium hexacarbonyl, and 0.16 mol per liter of triphenylarsine was heated at 160° C. in a stirred Hastelloy pressure vessel, under an atmosphere of carbon monoxide (continuous total pressure 700 psig; initial partial pressure of carbon monoxide 400 psig). G.C. (gas chromatography) analysis of the reaction mixture after a 4-hour reaction time showed it to contain 44.5% acetic anhydride, the balance being unreacted methyl acetate and the catalyst and promoter components.

EXAMPLE II

Example I was repeated except that 0.02 mol per liter of chromium di-iodide was used instead of chromium hexacarbonyl. After 4 hours of reaction, G.C. analysis showed the reaction mixture to contain 42.2% acetic anhydride.

EXAMPLE III

Example I was again repeated except that 0.02 mol per liter of chromium triacetate monohydrate was used instead of chromium hexacarbonyl. After 4 hours of reaction, G.C. analysis showed the reaction mixture to contain 40.7% acetic anhydride.

EXAMPLE IV

Example I was repeated except that there were used 0.32 mol per liter of triphenylarsine. G.C. analysis of the reaction mixture showed it to contain 58% acetic anhydride.

EXAMPLE V

Example I was again repeated using 0.16 mol/l of tri-p-tolyarsine instead of the triphenylarsine. G.C. analysis of the reaction mixture showed it contain 47.2% acetic anhydride.

EXAMPLE VI

Example I was repeated in a further experiment but 0.16 mol per liter of dimethylphenylarsine was substituted for the triphenylarsine. G.C. analysis of the reaction mixture after a 4-hour reaction time showed it to contain 39.1% acetic anhydride and, as in the preceding and succeeding examples, the balance being unreacted methyl acetate and the catalyst and promoter components.

EXAMPLE VII

Methyl acetate containing 0.01 mol per liter of rhodium trichloride hydrate, 0.02 mol per liter of chromium hexacarbonyl, 0.6 mol per liter of methyl iodide, and 0.16 mol per liter of methyldiphenylarsine was heated at 160° C. in a stirred Hastelloy pressure vessel under an atmosphere of carbon monoxide (continuous total pressure of 700 p.s.i.g.; initial carbon monoxide partial pressure 400 psig). G.C. analysis of the reaction mixture after a 4-hour reaction time showed it to contain 83% acetic anhydride.

COMPARATIVE EXAMPLE A

Example I was repeated as follows but using a phosphine. Methyl acetate containing 0.01 mol per liter of rhodium trichloride hydrate, 0.6 mol per liter of methyl iodide, 0.02 mol per liter of chromium hexacarbonyl, and 0.16 mol per liter of tri-n-butylphosphine was heated at 160° C. in a stirred Hastelloy pressure vessel, under an atmosphere of carbon monoxide (continuous total pressure 700 psig; initial partial pressure of carbon monoxide 400 psig). G.C. analysis of the reaction mixture after a 4-hour reaction time showed it to contain 21% acetic anhydride.

COMPARATIE EXAMPLE B

Comparative Example A was repeated using 0.16 mol/l of tri-n-butylarsine in place of the phosphine. G.C. analysis of the reaction mixture showed it to contain 23% acetic anhydride.

COMPARATIVE EXAMPLE C

Comparative Example A was again repeated except that 0.16 mol per liter of methyl diphenylphosphine was used instead of tri-n-butylphosphine. G.C. analysis of the reaction mixture after a 4-hour reaction time showed it to contain 24.5% acetic anhydride.

COMPARATIVE EXAMPLE D

Again repeating Comparative Example A, 0.16 mol per liter of dimethylphenylphosphine was substituted for tri-n-butylphosphine. G.C. analysis of the reaction mixture after a 4-hour reaction time showed it to contain 28.4% acetic anhydride.

COMPARATIVE EXAMPLE E

Repeating Comparative Example A but using 0.16 mol per liter of tri-p-tolylphosphine instead of tri-n-butylphosphine, produced a reaction mixture after a 4-hour reaction time which G.C. analysis showed to contain 25.7% acetic anhydride.

COMPARATIVE EXAMPLE F

In this Example, 0.16 mol per liter of triphenylphosphine was substituted for the tri-n-butylphosphine of Comparative Example A but the reaction was otherwise the same. G.C. analysis of the reaction mixture after a 4-hour reaction time showed it to contain 24.2% acetic anhydride.

COMPARATIVE EXAMPLE G

In two experiments, Comparative Example A was repeated except that triphenyl stibine and tri-n-butyl stibine in 0.16 mol per liter quantities were substituted for the tri-n-butylphosphine of Comparative Example A. G.C. analyses of the reaction mixtures each after a 4-hour reaction time showed, in the case of tri-n-butyl stibine no acetic anhydride produced and in the case of triphenyl stibine only 0.6% acetic anhydride.

What is claimed is:

1. In a process for the preparation of an anhydride of a monocarboxylic acid which comprises reacting carbon monoxide, a halide which is an iodide or bromide and a compound selected from the group consisting of a carboxylate ester and a hydrocarbyl ether under substantially anhydrous conditions in the presence of a Group VIII noble metal catalyst the improvement which comprises carrying out said process in the presence of a multiple promoter comprising at least one metal of Group VIB of the Periodic Table, or their compounds, an an arsine of the formula:

wherein R and $R^1$ are monocyclic aryl groups or alkyl groups and $R^2$ is the radical

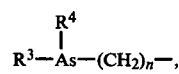

a momocyclic aryl group or an alkyl group, and wherein $R^3$ and $R^4$ are each a monocyclic aryl group or an alkyl group, with the proviso that at least one of R, $R^1$ and $R^2$ is a monocyclic aryl group, n being zero or a digit from 1–20, said reacting being carried out at a temperature of 25°–350° C. with a carbon monoxide partial pressure of 1–10,000 psi.

2. A process as defined in claim 1, wherein the Group VIII noble metal is rhodium.

3. A process as defined in claim 1, wherein the halide is a hydrocarbyl halide.

4. A process as defined in claim 1, wherein the metal component of the multiple promoter is chromium.

5. A process as defined in claim 1, wherein the arsine is selected from the group consisting of triphenylarsine, methyl diphenylarsine and dimethylphenylarsine.

6. A process as defined in claim 1, wherein the anhydride is acetic anhydride, the carboxylate ester is methyl acetate and the hydrocarbyl ether is dimethyl ether.

7. A process as defined in claim 6, wherein the Group VIII noble metal is rhodium.

8. A process as defined in claim 6, wherein the halide is a hydrocarbyl halide.

9. A process as defined in claim 6, wherein the metal component of the multiple promoter is chromium.

10. A process as defined in claim 6, wherein the arsine is selected from the group consisting of triphenylarsine, methyl diphenylarsine and dimethylphenylarsine.

* * * * *

UNITED STATES PATENT AND TRADEMARK OFFICE
CERTIFICATE OF CORRECTION

PATENT NO. : 4,251,458
DATED : Feb. 17, 1981
INVENTOR(S) : Joseph Pugach

It is certified that error appears in the above-identified patent and that said Letters Patent are hereby corrected as shown below:

Col. 1, line 18 - "drrawbacks" should be --drawbacks--

Col. 1, line 62 - "along" should be --alone--

Col. 2, line 37 - "onne" should be --one--

Col. 5, line 11 - "pre" should be --preferably--

Col. 5, line 32 - "acet cetonates" should be --acetylacetonates--

Col. 5, line 65 - "chronium" should be --chromium--

Col. 6, line 33 - "(tripenylarsine)" should be --(triphenylarsine)--

Col. 10, line 8 - the first "an" should be --and--

Col. 10, line 23 - "momocyclic" should be --monocyclic--

Signed and Sealed this

Twenth-eighth Day of September 1982

[SEAL]

Attest:

GERALD J. MOSSINGHOFF

Attesting Officer    Commissioner of Patents and Trademarks